US011865254B2

(12) United States Patent
Grychowski et al.

(10) Patent No.: US 11,865,254 B2
(45) Date of Patent: *Jan. 9, 2024

(54) OSCILLATING POSITIVE EXPIRATORY PRESSURE DEVICE

(71) Applicant: Trudell Medical International, London (CA)

(72) Inventors: Jerry Grychowski, Batavia, IL (US); Martin P. Foley, London (CA)

(73) Assignee: Trudell Medical International, London (CA)

( * ) Notice: Subject to any disclaimer, the term of this patent is extended or adjusted under 35 U.S.C. 154(b) by 928 days.

This patent is subject to a terminal disclaimer.

(21) Appl. No.: 16/853,089

(22) Filed: Apr. 20, 2020

(65) Prior Publication Data
US 2020/0297952 A1    Sep. 24, 2020

Related U.S. Application Data

(63) Continuation of application No. 15/651,706, filed on Jul. 17, 2017, now Pat. No. 10,668,238, which is a
(Continued)

(51) Int. Cl.
*A61M 16/08* (2006.01)
*A61M 16/00* (2006.01)
(Continued)

(52) U.S. Cl.
CPC ........ *A61M 16/0057* (2013.01); *A61M 11/02* (2013.01); *A61M 16/0006* (2014.02);
(Continued)

(58) Field of Classification Search
CPC ...... A61M 11/02; A61M 11/06; A61M 15/00; A61M 15/0016; A61M 15/0086;
(Continued)

(56) References Cited

U.S. PATENT DOCUMENTS 393,869 A    12/1888    Warren
938,808 A    11/1909    Yount
(Continued)

FOREIGN PATENT DOCUMENTS

EP    0 372 148 A1    6/1990
EP    0 678 306 A2    10/1995
(Continued)

OTHER PUBLICATIONS

U.S. Appl. No. 14/674,494, filed Mar. 31, 2015, Meyer et al.
(Continued)

*Primary Examiner* — Annette Dixon
(74) *Attorney, Agent, or Firm* — Crowell & Moring LLP

(57) ABSTRACT

An oscillating positive expiratory pressure apparatus having a housing defining a chamber, a chamber inlet, a chamber outlet, a deformable restrictor member positioned in an exhalation flow path between the chamber inlet and the chamber outlet, and an oscillation member disposed within the chamber. The deformable restrictor member and the oscillation member are moveable between an engaged position, where the oscillation member is in contact with the deformable restrictor member and an disengaged position, where the oscillation member is not in contact with the deformable restrictor member. The deformable restrictor member and the oscillation member move from the engaged position to the disengaged position in response to a first exhalation pressure at the chamber inlet, and move from the disengaged position to an engaged position in response to a second exhalation pressure at the chamber inlet.

19 Claims, 13 Drawing Sheets

Related U.S. Application Data continuation of application No. 13/959,293, filed on Aug. 5, 2013, now Pat. No. 9,737,677, which is a continuation of application No. 13/674,340, filed on Nov. 12, 2012, now Pat. No. 8,985,111, which is a continuation of application No. 12/607,496, filed on Oct. 28, 2009, now Pat. No. 8,327,849.

(60) Provisional application No. 61/109,075, filed on Oct. 28, 2008.

(51) Int. Cl.
  *A61M 16/20* (2006.01)
  *A61M 16/14* (2006.01)
  *A61M 11/02* (2006.01)
  *A61M 16/06* (2006.01)

(52) U.S. Cl.
  CPC ........ *A61M 16/06* (2013.01); *A61M 16/0816* (2013.01); *A61M 16/0866* (2014.02); *A61M 16/14* (2013.01); *A61M 16/208* (2013.01); *A61M 2205/10* (2013.01); *Y10S 137/908* (2013.01)

(58) Field of Classification Search
  CPC .............. A61M 15/0098; A61M 16/00; A61M 16/0006; A61M 16/0057; A61M 16/0066; A61M 16/0096; A61M 16/06; A61M 16/08; A61M 16/0808; A61M 16/0816; A61M 16/0833; A61M 16/0866; A61M 16/14; A61M 16/20; A61M 16/205; A61M 16/208; A61M 16/209; A61M 2205/10; A63B 2071/0633; A63B 21/00069; A63B 21/00076; A63B 21/00196; A63B 23/18; Y10S 128/912; Y10S 137/908
  See application file for complete search history.

(56) References Cited

U.S. PATENT DOCUMENTS

| | | |
|---|---|---|
| 2,670,739 A | 3/1954 | NcNeill |
| 2,918,917 A | 12/1959 | Emerson |
| 3,710,780 A | 1/1973 | Milch |
| 3,908,987 A | 9/1975 | Boehringer |
| 4,054,134 A | 10/1977 | Kritzer |
| 4,062,358 A | 12/1977 | Kritzer |
| 4,182,366 A | 1/1980 | Boehringer |
| 4,198,969 A | 4/1980 | Virag |
| 4,221,381 A | 9/1980 | Ericson |
| 4,226,233 A | 10/1980 | Kritzer |
| 4,231,375 A | 11/1980 | Boehringer et al. |
| 4,267,832 A | 5/1981 | Hakkinen |
| 4,275,722 A | 6/1981 | Sorensen |
| 4,298,023 A | 11/1981 | McGinnis |
| 4,327,740 A | 5/1982 | Shuman |
| 4,403,616 A | 9/1983 | King |
| 4,436,090 A | 3/1984 | Darling |
| 4,470,412 A | 9/1984 | Nowacki et al. |
| 4,601,465 A | 7/1986 | Roy |
| 4,611,591 A | 9/1986 | Inui et al. |
| 4,635,631 A | 1/1987 | Izumi |
| 4,651,731 A | 3/1987 | Vicenzi et al. |
| 4,739,987 A | 4/1988 | Nicholson |
| 4,770,413 A | 9/1988 | Green |
| 4,951,661 A * | 8/1990 | Sladek .............. A61M 16/0808 128/205.24 |
| 4,973,047 A | 11/1990 | Norell |
| 4,981,295 A | 1/1991 | Belman et al. |
| 5,018,517 A | 5/1991 | Liardet |
| 5,042,467 A | 8/1991 | Foley |
| 5,065,746 A | 11/1991 | Steen |
| 5,193,529 A | 3/1993 | Labaere |
| 5,345,930 A | 9/1994 | Cardinal et al. |
| 5,372,128 A | 12/1994 | Haber et al. |
| 5,381,789 A | 1/1995 | Marquardt |
| 5,451,190 A | 9/1995 | Liardet |
| 5,479,920 A | 1/1996 | Piper et al. |
| 5,540,220 A | 7/1996 | Gropper et al. |
| 5,569,122 A | 10/1996 | Cegla |
| 5,570,682 A | 11/1996 | Johnson |
| 5,598,839 A | 2/1997 | Niles et al. |
| 5,613,489 A | 3/1997 | Miller |
| 5,645,049 A | 7/1997 | Foley et al. |
| 5,647,345 A | 7/1997 | Saul |
| 5,655,520 A | 8/1997 | Howe |
| 5,658,221 A | 8/1997 | Hougen |
| 5,727,546 A | 3/1998 | Clarke et al. |
| 5,791,339 A | 8/1998 | Winter |
| 5,829,429 A | 11/1998 | Hughes |
| 5,848,588 A | 12/1998 | Foley et al. |
| 5,862,802 A | 1/1999 | Bird |
| 5,890,998 A | 4/1999 | Hougen |
| 5,893,361 A | 4/1999 | Hughes |
| 5,899,832 A | 5/1999 | Hougen |
| 5,910,071 A | 6/1999 | Hougen |
| 5,925,831 A | 7/1999 | Storsved |
| 5,988,166 A | 11/1999 | Hayek |
| 6,026,807 A | 2/2000 | Puderbaugh et al. |
| 6,029,661 A | 2/2000 | Whaley et al. |
| 6,044,841 A | 4/2000 | Verdun et al. |
| 6,058,932 A | 5/2000 | Hughes |
| 6,066,101 A | 5/2000 | Johnson |
| 6,067,984 A | 5/2000 | Piper |
| 6,083,141 A | 7/2000 | Hougen |
| 6,089,105 A | 7/2000 | Ricciardelli |
| 6,102,038 A | 8/2000 | DeVries |
| 6,167,881 B1 | 1/2001 | Hughes |
| 6,176,235 B1 | 1/2001 | Benarrouch et al. |
| 6,182,657 B1 | 2/2001 | Brydon et al. |
| D440,651 S | 4/2001 | Foran |
| 6,240,917 B1 | 6/2001 | Andrade |
| 6,253,766 B1 | 7/2001 | Niles |
| 6,269,839 B1 | 8/2001 | Wickham et al. |
| 6,293,279 B1 | 9/2001 | Schmidt et al. |
| 6,340,025 B1 | 1/2002 | Van Brunt |
| 6,345,617 B1 | 2/2002 | Engelbreth et al. |
| 6,412,481 B1 | 7/2002 | Bienvenu et al. |
| 6,446,629 B1 | 9/2002 | Takaki et al. |
| 6,447,459 B1 | 9/2002 | Larom |
| 6,500,095 B1 | 12/2002 | Hougen |
| 6,557,549 B2 | 5/2003 | Schmidt et al. |
| 6,581,595 B1 | 6/2003 | Murdock et al. |
| 6,581,596 B1 | 6/2003 | Truitt |
| 6,581,598 B1 | 6/2003 | Foran et al. |
| 6,581,600 B2 | 6/2003 | Bird |
| 6,595,203 B1 | 7/2003 | Bird |
| 6,606,989 B1 | 8/2003 | Brand |
| 6,607,008 B1 | 8/2003 | Yoshimoto et al. |
| 6,615,831 B1 | 9/2003 | Truitt |
| 6,631,721 B1 | 10/2003 | Salter et al. |
| 6,659,100 B2 | 12/2003 | O'Rourke |
| 6,681,768 B2 | 1/2004 | Haaije de Boer et al. |
| 6,702,769 B1 | 3/2004 | Fowler-Hawkins |
| 6,708,690 B1 | 3/2004 | Hete et al. |
| 6,708,691 B1 | 3/2004 | Hayek |
| 6,726,598 B1 | 4/2004 | Jarvis |
| D490,519 S | 5/2004 | Pelerossi et al. |
| 6,776,159 B2 | 8/2004 | Pelerossi et al. |
| 6,848,443 B2 | 2/2005 | Schmidt et al. |
| 6,851,425 B2 | 2/2005 | Jaffre |
| 6,904,906 B2 | 6/2005 | Salter |
| 6,923,181 B2 | 8/2005 | Tuck |
| 6,929,007 B2 | 8/2005 | Emerson |
| 6,984,214 B2 | 1/2006 | Fowler-Hawkins |
| 7,059,324 B2 | 6/2006 | Pelerossi et al. |
| 7,096,866 B2 | 8/2006 | Be'eri et al. |
| 7,134,434 B2 | 11/2006 | Truitt et al. |
| 7,165,547 B2 | 1/2007 | Truitt et al. |
| 7,188,621 B2 | 3/2007 | DeVries |
| 7,191,776 B2 | 3/2007 | Niles |

(56) References Cited

U.S. PATENT DOCUMENTS

| | | |
|---|---|---|
| 7,191,780 B2 | 3/2007 | Faram |
| 7,214,170 B2 | 5/2007 | Summers et al. |
| 7,383,740 B2 | 6/2008 | Krasilchikov et al. |
| 7,617,821 B2 | 11/2009 | Hughes |
| 7,699,054 B2 | 4/2010 | Pelerossi et al. |
| 7,717,847 B2 | 5/2010 | Smith |
| 7,771,472 B2 | 8/2010 | Hendricksen |
| 7,779,841 B2 | 8/2010 | Dunsmore et al. |
| 7,798,148 B2 | 9/2010 | Doshi |
| 7,856,979 B2 | 12/2010 | Doshi |
| 7,905,228 B2 | 3/2011 | Blacker et al. |
| 7,909,033 B2 | 3/2011 | Faram |
| 8,006,922 B2 | 8/2011 | Katzer |
| 8,025,051 B2 | 9/2011 | Dagsland |
| 8,025,054 B2 | 9/2011 | Dunsmore et al. |
| 8,043,236 B2 | 10/2011 | Goldshtein et al. |
| 8,051,854 B2 | 11/2011 | Faram |
| RE43,174 E | 2/2012 | Schmidt et al. |
| 8,118,024 B2 | 2/2012 | DeVries et al. |
| 8,118,713 B2 | 2/2012 | Foley et al. |
| 8,225,785 B2 | 7/2012 | Richards et al. |
| 8,327,849 B2 | 12/2012 | Grychowski et al. |
| 8,360,061 B2 | 1/2013 | Brown |
| 8,460,223 B2 | 6/2013 | Huster et al. |
| 8,469,029 B2 | 6/2013 | Brown et al. |
| 8,485,179 B1 * | 7/2013 | Meyer .................. A61M 16/00 128/200.24 |
| 8,528,547 B2 | 9/2013 | Dunsmore |
| 8,539,951 B1 | 9/2013 | Meyer et al. |
| 8,985,111 B2 | 3/2015 | Grychowski et al. |
| 8,993,774 B2 | 3/2015 | Kanbara et al. |
| D731,050 S | 6/2015 | Meyer |
| 9,149,589 B2 | 10/2015 | Meyer et al. |
| 9,220,855 B2 | 12/2015 | Meyer |
| 9,358,417 B2 | 6/2016 | Meyer |
| 9,517,315 B2 | 12/2016 | Meyer |
| D776,804 S | 1/2017 | Meyer |
| D778,429 S | 2/2017 | Engelbreth et al. |
| D780,906 S | 3/2017 | Engelbreth et al. |
| 9,636,473 B2 * | 5/2017 | Meyer ................. A61M 16/208 |
| 9,737,677 B2 * | 8/2017 | Grychowski ......... A61M 16/06 |
| 9,808,588 B1 | 11/2017 | Meyer et al. |
| 9,849,257 B2 | 12/2017 | Meyer et al. |
| 9,913,955 B2 * | 3/2018 | Grychowski ......... A61M 16/06 |
| 9,950,128 B2 | 4/2018 | Meyer et al. |
| 9,981,106 B2 | 5/2018 | Meyer et al. |
| 10,039,691 B2 | 8/2018 | Von Hollen |
| 10,076,616 B2 | 9/2018 | Meyer et al. |
| 10,272,224 B2 | 4/2019 | Costella et al. |
| 10,363,383 B2 | 7/2019 | Alizoti et al. |
| 10,413,698 B2 | 9/2019 | Meyer et al. |
| 10,449,324 B2 | 10/2019 | Meyer et al. |
| 2003/0234017 A1 * | 12/2003 | Pelerossi .......... A63B 21/00076 128/201.28 |
| 2006/0032607 A1 | 2/2006 | Wisniewski |
| 2007/0089740 A1 | 4/2007 | Baumert et al. |
| 2007/0259759 A1 | 11/2007 | Sumners et al. |
| 2008/0078383 A1 * | 4/2008 | Richards ............. A61M 16/209 128/203.12 |
| 2008/0257348 A1 | 10/2008 | Piper |
| 2009/0241949 A1 | 10/2009 | Smutney et al. |
| 2010/0139655 A1 | 6/2010 | Genosar |
| 2010/0307487 A1 | 12/2010 | Dunsmore et al. |
| 2012/0097164 A1 | 4/2012 | Rozario et al. |
| 2015/0374939 A1 | 12/2015 | Meyer et al. |
| 2017/0049979 A1 | 2/2017 | Meyer et al. |
| 2017/0128683 A1 | 5/2017 | Meyer et al. |
| 2017/0312461 A1 | 11/2017 | Grychowski et al. |
| 2018/0154093 A1 | 6/2018 | Meyer et al. |
| 2018/0214662 A1 | 8/2018 | Meyer et al. |
| 2018/0256839 A1 | 9/2018 | Meyer et al. |
| 2019/0240533 A1 | 8/2019 | Alizoti |

FOREIGN PATENT DOCUMENTS

| | | |
|---|---|---|
| EP | 1 464 357 A1 | 10/2004 |
| EP | 1 435 251 B1 | 6/2006 |
| EP | 1 103 287 B1 | 6/2007 |
| EP | 1 897 576 A1 | 3/2008 |
| EP | 1 908 489 A1 | 4/2008 |
| EP | 2444114 A1 | 4/2012 |
| EP | 2455137 A2 | 5/2012 |
| GB | 2 425 488 A | 11/2006 |
| WO | WO 1989/03707 A1 | 5/1989 |
| WO | WO 1996/40376 A1 | 12/1996 |
| WO | WO 1999/16490 A1 | 4/1999 |
| WO | WO 2000/27455 A1 | 5/2000 |
| WO | WO 2007/061648 A3 | 5/2007 |
| WO | WO 2007/119104 A3 | 10/2007 |
| WO | WO 2008/063966 A1 | 5/2008 |
| WO | WO 2008/122045 A1 | 10/2008 |
| WO | WO 2009/131965 | 10/2009 |
| WO | WO 2011/058470 | 5/2011 |
| WO | WO 2012/038864 A2 | 3/2012 |
| WO | WO 2016/012740 | 1/2016 |

OTHER PUBLICATIONS

Web page entitled Bronchial Hygiene, acapella Vibratory PEP Therapy System accessed from http://www.smiths-medical.com/catalog/bronchial-hygiene/acapella/acapella.html on Jul. 7, 2009.

Web page entitled Thayer Quake accessed from http://www.thayermedical.com/quake.htm on Jul. 7, 2009.

Human growth hormone, cortisol, and acid-base balance changes after hyperventilation and breath-holding; PubMed—indexed for MEDLINE; Int J Sports Med., Dec. 1986; 7(6):311-5, Djarova T.

Bosco C, Cardinale M. & Tsarpela O (1999). Influence of vibration on mechanical power and electromyogram activity in human arm flexor muscles. Eur J Appl Physiol 79, 306-311.

David Sumners; Power Breathing and Strength; http://EzineArticles.com/972576 Published: Feb. 7, 2008.

Good Vibrations blog; http://vibrotraining.blogspot.com, Earliest posting Jan. 17, 2008.

Breathtaking News; More Youbreathe; Aug. 10, 2007.

PCT International Search Report for PCT/IB2012/001089, dated Oct. 5, 2012.

PCT International Written Opinion for PCT/IB2012/001089, dated Oct. 5, 2012.

Preliminary Report on Patentability, PCT/IB2012/001089, dated Dec. 10, 2013.

PCT/IB2012001089 European Search Report dated Nov. 6, 2014.

*D R Burton Healthcare LLC v. Trudell Medical International*; "Petition for Inter Partes Review of Claims 1-26 Under 35 U.S.C. §§ 311-319 and 37 C.F.R. § 42.100 et seq.";U.S. Pat. No. 9,808,588; May 4, 2018; 94 pages.

*D R Burton Healthcare LLC v. Trudell Medical International*; "Declaration of Dr. William W. Durgin, Ph.D., In Support of Patent Owner's Preliminary Response to Petition for Inter Partes Review"; Case No. IPR2018-01025, U.S. Pat. No. 9,808,588; Trudell Medical Exhibit 2001-00001-2001-00217; Sep. 6, 2018; 217 pages.

*D R Burton Healthcare LLC v. Trudell Medical International*; "Patent Owner's Preliminary Response to Petition for Inter Partes Review"; Case No. IPR2018-01025, U.S. Pat. No. 9,808,588; Sep. 7, 2018; 107 pages.

*D R Burton Healthcare LLC v. Trudell Medical International*; "Petitioner's Reply to Patent Owner Preliminary Response"; Case No. IPR2018-01025, U.S. Pat. No. 9,808,588 B1; Oct. 9, 2018; 16 pages.

*D R Burton Healthcare LLC v. Trudell Medical International*; "Decision Denying Institution of Inter Partes Review"; Case No. IPR2018-01025, U.S. Pat. No. 9,808,588 B1; Nov. 29, 2018; 32 pages.

* cited by examiner

OSCILLATING POSITIVE EXPIRATORY PRESSURE DEVICE

RELATED APPLICATIONS

This application is a continuation of U.S. application Ser. No. 15/651,706, filed on Jul. 17, 2017, which is a continuation of U.S. application Ser. No. 13/959,293, filed on Aug. 5, 2013, now U.S. Pat. No. 9,737,677, which is a continuation of U.S. application Ser. No. 13/674,340, filed on Nov. 12, 2012, now U.S. Pat. No. 8,985,111, which is a continuation of U.S. application Ser. No. 12/607,496, filed on Oct. 28, 2009, now U.S. Pat. No. 8,327,849, which claims the benefit of U.S. Provisional Application No. 61/109,075, filed on Oct. 28, 2008, all of which are incorporated herein by reference.

TECHNICAL FIELD

The present disclosure relates to an expiratory treatment device, and in particular, to an oscillating positive expiratory pressure ("OPEP") device.

BACKGROUND

Each day, humans may produce upwards of 30 milliliters of sputum, which is a type of bronchial secretion. Normally, an effective cough is sufficient to loosen secretions and clear them from the body's airways. However, for individuals suffering from more significant bronchial obstructions, such as collapsed airways, a single cough may be insufficient to clear the obstructions.

OPEP therapy represents an effective bronchial hygiene technique for the removal of bronchial secretions in the human body and is an important aspect in the treatment and continuing care of patients with bronchial obstructions, such as those suffering from chronic obstructive lung disease. It is believed that OPEP therapy, or the oscillation of exhalation pressure at the mouth during exhalation, effectively transmits an oscillating back pressure to the lungs, thereby splitting open obstructed airways and loosening the secretions contributing to bronchial obstructions.

OPEP therapy is an attractive form of treatment because it can be easily taught to most hospitalized patients, and such patients can assume responsibility for the administration of OPEP therapy throughout their hospitalization and also once they have returned home. To that end, a number of portable OPEP devices have been developed.

BRIEF SUMMARY

A portable OPEP device and a method of performing OPEP therapy is described herein. In one aspect, a portable OPEP device includes a housing defining a chamber, a chamber inlet configured to receive exhaled air into the chamber, a chamber outlet configured to permit exhaled air to exit the chamber, a deformable restrictor member positioned in an exhalation flow path between the chamber inlet and the chamber outlet, and an oscillation member disposed within the chamber. The deformable restrictor member and the oscillation member are moveable relative to one another between an engaged position, where the oscillation member is in contact with the deformable restrictor member and a disengaged position, where the oscillation member is not in contact with the deformable restrictor member. The deformable restrictor member and the oscillation member are also configured to move from the engaged position to the disengaged position in response to a first exhalation pressure at the chamber inlet, and move from the disengaged position to an engaged position in response to a second exhalation pressure at the chamber inlet. The first exhalation pressure is greater than the second exhalation pressure.

In another aspect, the deformable restrictor member deforms in response to an intermediate exhalation pressure at the chamber inlet, and returns to a natural shape in response to the first exhalation pressure at the chamber inlet.

In another aspect, the OPEP device has a biasing member positioned to bias the deformable restrictor member and the oscillation member to the engaged position. The biasing member may be a spring. Alternatively, the biasing member may have at least one pair of magnets, wherein a first magnet of the at least one pair of magnets is connected to the oscillation member and a second magnet of the at least one pair of magnets is connected to the housing. The position of the biasing member may also be selectively moveable to adjust the amount of bias In yet another aspect, the OPEP device includes a glide surface extending from the housing into the chamber, such that the glide surface is in sliding contact about the oscillation member, and movement of the oscillation member is substantially limited to reciprocal movement about an axis of the oscillation member.

In another aspect, the oscillation member includes at least one channel adapted so that the exhalation flow path is not completely restricted when the deformable restrictor member and the oscillation member are in the engaged positioned.

In another aspect, the OPEP device includes a mouthpiece connected to the housing that is in fluid communication with the chamber inlet. The mouthpiece may have a cross-sectional area greater than a cross-sectional area of the chamber inlet.

In yet another aspect, the housing has a first portion and a second portion, with the second portion being removably connected to the first portion.

In another aspect, the OPEP device includes a respiratory portal for receiving an aerosol medicament. Additionally, the oscillation member may comprise a one-way valve configured to permit the aerosol medicament to enter the chamber through the respiratory portal, the respiratory portal being in fluid communication with the chamber inlet when the one-way valve is open.

In another aspect, a method of performing oscillating positive expiratory pressure therapy is provided. The method includes passing a flow of exhaled air along an exhalation flow path defined between an inlet and an outlet of a chamber in an oscillating positive expiratory pressure device. The method also includes restricting the flow of exhaled air by maintaining a deformable restrictor member and an oscillation member disposed within the chamber in an engaged position, where the oscillation member is in contact with the deformable restrictor member, until a first exhalation pressure is reached at a chamber inlet. The method further includes unrestricting the flow of exhaled air by moving the deformable restrictor member and the oscillation member to a disengaged position, where the oscillation member is not in contact with the deformable restrictor member, until a second exhalation pressure is reached at the chamber inlet. The method also includes returning the deformable restrictor member and the oscillation member to the engaged position with a biasing force when the second exhalation pressure is reached at the chamber inlet. The first exhalation pressure may be greater than the second exhalation pressure. Finally, the method may also include deforming the deformable restrictor member in response to an intermediate exhalation pressure at the chamber inlet, and returning the deformable restrictor member to a natural shape in response to the first exhalation pressure at the chamber inlet.

In another embodiment, a system for providing oscillating positive expiratory pressure therapy in combination with aerosol therapy is provided. The system includes an oscillating positive expiratory pressure apparatus having a housing defining a chamber, a chamber inlet configured to receive exhaled air into the chamber, and a chamber outlet configured to permit exhaled air to exit the chamber. The oscillating positive expiratory pressure apparatus also has an exhalation flow path defined between the chamber inlet and the chamber outlet, and an oscillation member disposed within the chamber and configured to operatively restrict a flow of exhaled air along the exhalation flow path. The oscillation member is moveable relative to the flow path between a restrictive position, where the flow of exhaled air is substantially restricted and an unrestrictive position, where the flow of exhaled air is substantially unrestricted. The oscillating positive expiratory pressure apparatus may also have a respiratory portal for receiving an aerosol medicament. The respiratory portal may be in fluid communication with the chamber inlet. The system also includes an aerosol therapy apparatus removably connected to the respiratory portal of the oscillating positive expiratory pressure apparatus. The aerosol therapy apparatus includes an aerosol housing having an aerosol chamber for holding an aerosol medicament, and an aerosol outlet communicating with the aerosol chamber for permitting the aerosol medicament to be withdrawn from the aerosol chamber.

DESCRIPTION OF THE PREFERRED EMBODIMENTS

OPEP therapy is very effective within a specific range of operating conditions. For example, an adult human may have an exhalation flow rate ranging from 10 to 60 liters per minute, and may maintain a static exhalation pressure in the range of 10 to 20 cm $H_2O$. Within these parameters, OPEP therapy is believed to be most effective when changes in the exhalation pressure range from 5 to 20 cm $H_2O$ oscillating at a frequency of 10 to 40 Hz. In contrast, an infant may have a much lower exhalation flow rate, and may maintain a lower static exhalation pressure, thereby altering the operating conditions most effective for OPEP therapy. As described below, the present invention is configurable so that ideal operating conditions may be selected and maintained.

Figure 1:
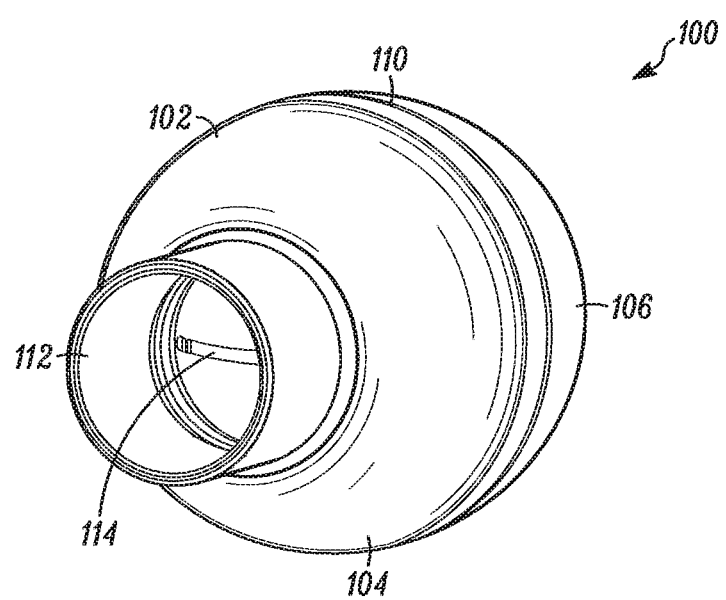
FIG. 1 is a front perspective view of a first embodiment of an OPEP device.

Referring to FIG. 1, a first embodiment of an assembled OPEP device 100 is shown. The OPEP device 100 comprises a housing 102 having a front portion 104 and a rear portion 106 which together defines a chamber 108 (see FIG. 3). The housing 102 may be constructed of any durable material, such as a plastic or a metal. The OPEP device 100 shown in FIG. 1 is substantially spherical in shape, which provides for an easy grasp of the OPEP device 100 in the hands of a user, as well as portability. It should be appreciated, however, that the OPEP device 100 could be any shape, so long as it defines a chamber 108 capable of housing the necessary components, as described herein. Preferably, the housing 102 is openable so the chamber 108 may be accessed for cleaning and replacing components contained therein. As shown, the front portion 104 and the rear portion 106 of the housing 102 are removably connected along a joint 110, such as by a snap fit or a threaded screw connection.

The OPEP device 100 also includes a mouthpiece 112 which may either be formed as an integral part of the housing 102 or removably attached to the housing 102. Although the mouthpiece 112 is shown as being cylindrical in shape, the mouthpiece 112 could be any number of alternative sizes or shapes to accommodate various users of the OPEP device 100, such as children or adults. A chamber inlet 114 positioned within the mouthpiece 112 is configured to receive exhaled air into the chamber 108. In view of the description below, it should be apparent that the cross sectional area of the chamber inlet 114 is an important variable affecting the exhalation pressure generated at the mouth of a user, and may be modified or selectively replaced according to the desired operating conditions.

Figure 2:
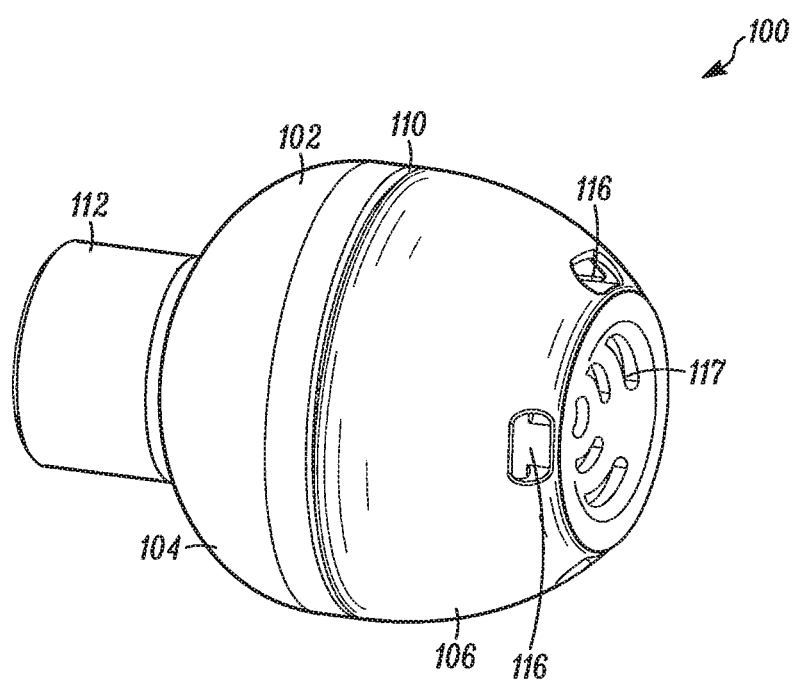
FIG. 2 is a side perspective view of the embodiment of FIG. 1.

A side perspective view of the OPEP device 100 is shown in FIG. 2. The OPEP device 100 further comprises at least one chamber outlet 116 configured to permit exhaled air to exit the chamber 108. The at least one chamber outlet 116 may comprise any number of apertures, having any shape or size. Furthermore, the at least one chamber outlet 116 may be located elsewhere on the housing 102. The OPEP device 100 may also include a grate 117 to prevent unwanted objects from entering housing 102.

Figure 3:
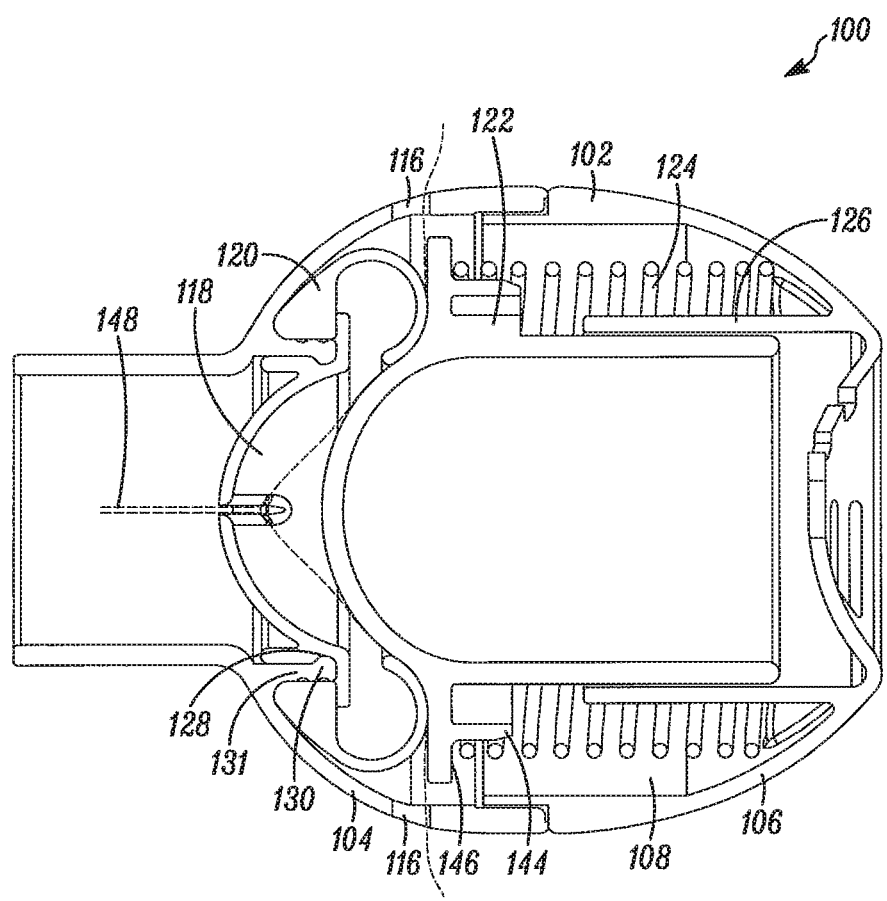
FIG. 3 is a cross-sectional side view of the embodiment of FIG. 1, showing a deformable restrictor member and an oscillation member in an engaged position.

Referring to FIG. 3, a cross-sectional side view of the OPEP device 100 shows the internal components of the OPEP device 100. The minimal number of components contained in the OPEP device 100, and its relatively simple operation, make the OPEP device 100 particularly suitable for single patient use. In general, the housing 102 of the OPEP device 100 encloses an inlet insert 118, a deformable restrictor member 120, an oscillation member 122, a coil spring 124, and a glide surface 126. As explained below, the various alternatives for each of the inlet insert 118, the deformable restrictor member 120, the oscillation member 122, and the coil spring 124 provide of a highly configurable OPEP device 100.

Figure 4:
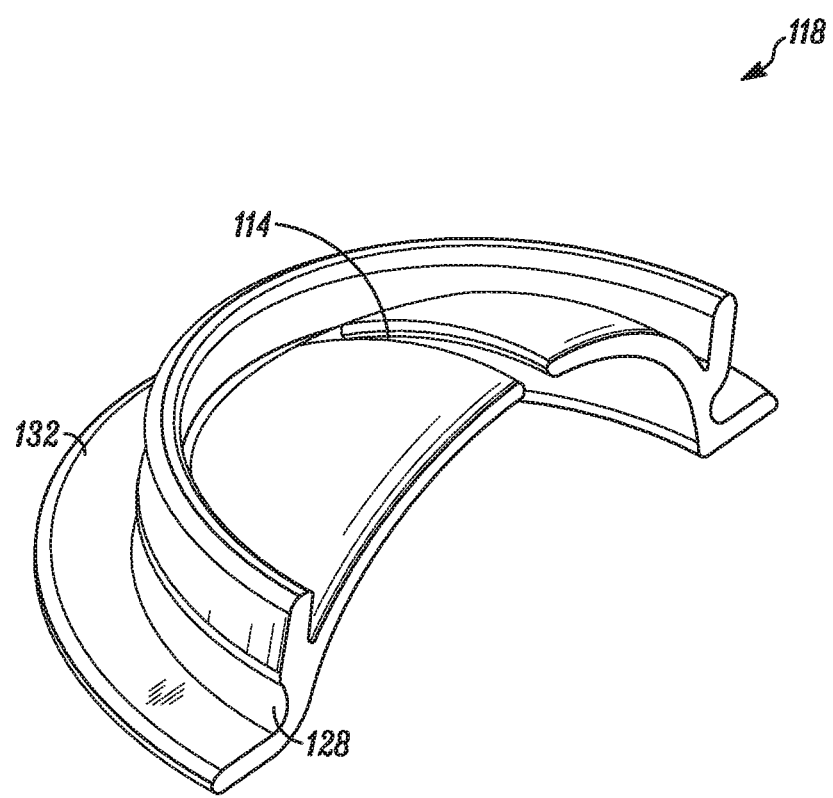
FIG. 4 is a cross-sectional perspective view of an inlet insert shown in the embodiment of FIG. 1.

A cross-sectional perspective view of the inlet insert 118 is shown in FIG. 4. The inlet insert 118 is removably connectable to the housing 102 and/or mouthpiece 112 of the OPEP device 100, and includes the chamber inlet 114. The chamber inlet 114 may be a single narrow aperture, or alternatively, may comprise any number of apertures having any size or shape. Because the inlet insert 118 is removably connectable to the OPEP device 100, a user may select an inlet insert 118 having the appropriate sized chamber inlet 114 for the prescribed OPEP therapy. It is important, however, that the mouthpiece 112 have a cross-sectional area greater than the cross-sectional area of the chamber inlet 114.

The inlet insert 118 is configured to be snap or compression fit within the front portion 104 of the housing 102, which may be accomplished while the front portion 104 and the rear portion 106 are detached. The inlet insert 118 includes an annular recess 128 for receiving a corresponding annular protrusion 130, which may be located on a rim 131 connected to either the mouthpiece 112 or the housing 102, as shown in FIG. 4. Furthermore, the inlet insert 118 is shaped to fit within the spherically shaped OPEP device 100; however, the inlet insert 118 could be modified to fit within any other shaped OPEP device. Alternatively, the inlet insert 118 and the chamber inlet 114 may be formed as an integral part of the housing 102 or the mouthpiece 112. The inlet insert 118 further includes an annular mounting surface 132 for supporting the deformable restrictor member 120, as described below.

Figure 5:
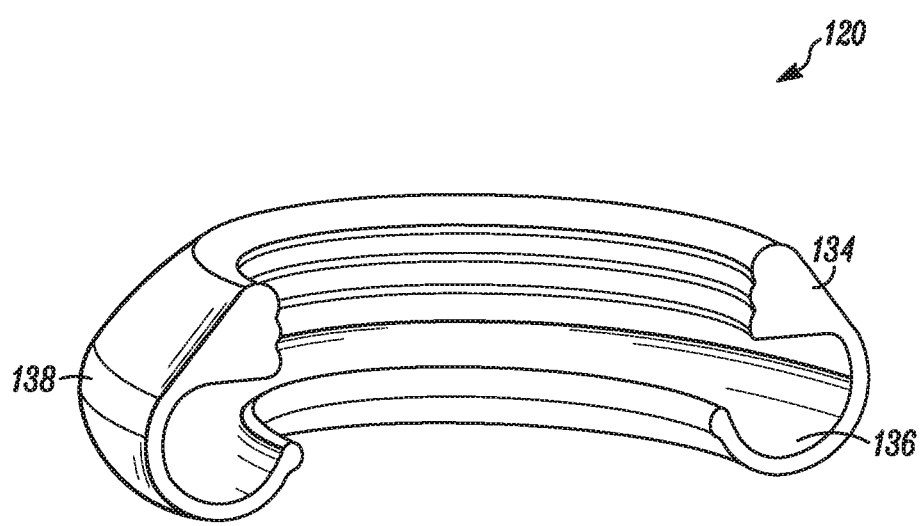
FIG. 5 is a cross-sectional perspective view of a deformable restrictor member shown in the embodiment of FIG. 1.

Referring to FIG. 5, a cross-sectional perspective view of the deformable restrictor member 120 is shown. The deformable restrictor member 120 operates as a regulator of the exhalation pressure at the chamber inlet 114. The deformable restrictor member 120 may be constructed of an elastic material, preferably having an elasticity of at least 40 durometers (A scale). Like the inlet insert 118, the deformable restrictor member 120 may be any number of shapes, but is shown in FIG. 5 as being circular to fit within the spherically shaped OPEP device 100.

The deformable restrictor member 120 generally includes an upper portion 134, a lower portion 136, and a reinforcing band 138 of elastic material. As shown in FIG. 3, the upper portion 134 is configured for mounting the deformable restrictor member 120 on the mounting surface 132 and about the rim 131, as explained above. When the front portion 104 and the rear portion 106 of the housing 102 are detached, the upper portion 134 of the deformable restrictor member 120 is mountable about the rim 131 of the inlet insert 118, and the inlet insert 118 may be snapped into place within the housing 102. Once the inlet insert 118 is connected to the housing 102, the deformable restrictor member 120 is retained by the rim 131, the mounting surface 132, and the front portion 104 of the housing 102. Alternatively, the housing 102 or the mouthpiece 112 may be configured to provide the rim 131 and the mounting surface 132 for mounting and retaining the deformable restrictor member 120.

The deformable restrictor member 120, and in particular, the lower portion 136, is configured to deform as the exhalation pressure at the chamber inlet 114 increases. Preferably, the lower portion 136 of the deformable restrictor member 120 should be curved inward so that, as the deformable restrictor member 120 deforms, the lower portion 136 expands in a direction away from the upper portion 134. To improve the elasticity and rigidity of the deformable restrictor member 120, a reinforcing band 138 of elastic material may be added to the deformable restrictor member 120. Depending on the shape of the deformable restrictor member 120 and the desired elasticity, the reinforcing band 138 may be omitted or located elsewhere on the deformable restrictor member 120.

Figure 6:
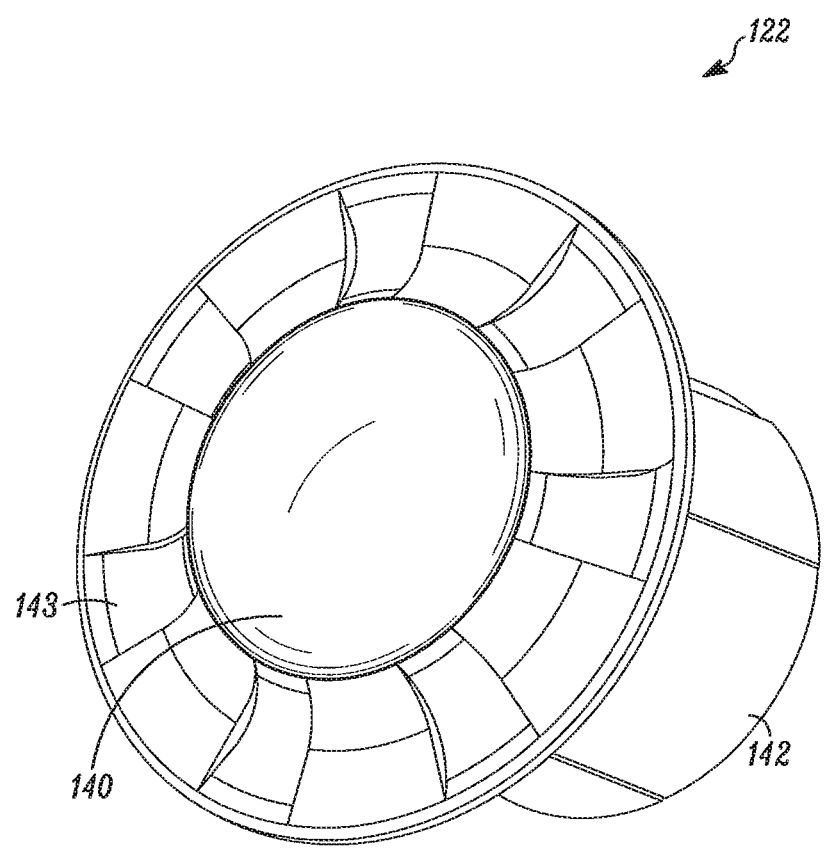
FIG. 6 is a front perspective view of an oscillation member shown in the embodiment of FIG. 3.

Referring to FIG. 6, a front perspective view of an oscillation member 122 is shown. In general, the oscillation member 122 includes a contact surface 140 connected to the end of a post 142. The contact surface 140 is configured to engage the lower portion 136 of the deformable restrictor member 120. As shown in FIGS. 3 and 6, the contact surface 140 may be hemispherically shaped to fit within a correspondingly shaped portion of the inlet insert 118, or a correspondingly shaped portion of the housing 102 or mouthpiece 112 if the inlet insert 118 is omitted. Alternatively, the contact surface 140 may be substantially flat.

The contact surface 140 shown in FIG. 6 includes at least one channel 143 which traverses a portion of the contact surface 140 where the deformable restrictor member 120 and the oscillation member 122 engage one another. In this embodiment, the channels 143 are sized such that an air passage from the chamber inlet 114 to the chamber outlet 116 is maintained during both inhalation and exhalation via the space defined by the restrictor member 120 and the channels 143. This air passage, or collection of air passages, is sized to prevent complete restriction of air flow but selected to allow sufficient build-up of pressure to provide oscillating pressure upon patient exhalation.

Although the contact surface 140 is shown in FIG. 6 as having seven separate channels 143, the contact surface 140 could include any number of channels 143. Furthermore, the one or more channels 143 may have a variety of sizes, depending upon the desired restriction of exhaled air received from the user. Alternatively, the contact surface 140 may be fabricated without any channels 143. Because the oscillation member 122 is removably enclosed within the housing 102 of the OPEP device 100, a user may select an oscillation member 122 having the appropriate shape, size, or number of channels for the prescribed OPEP therapy.

Figure 7:
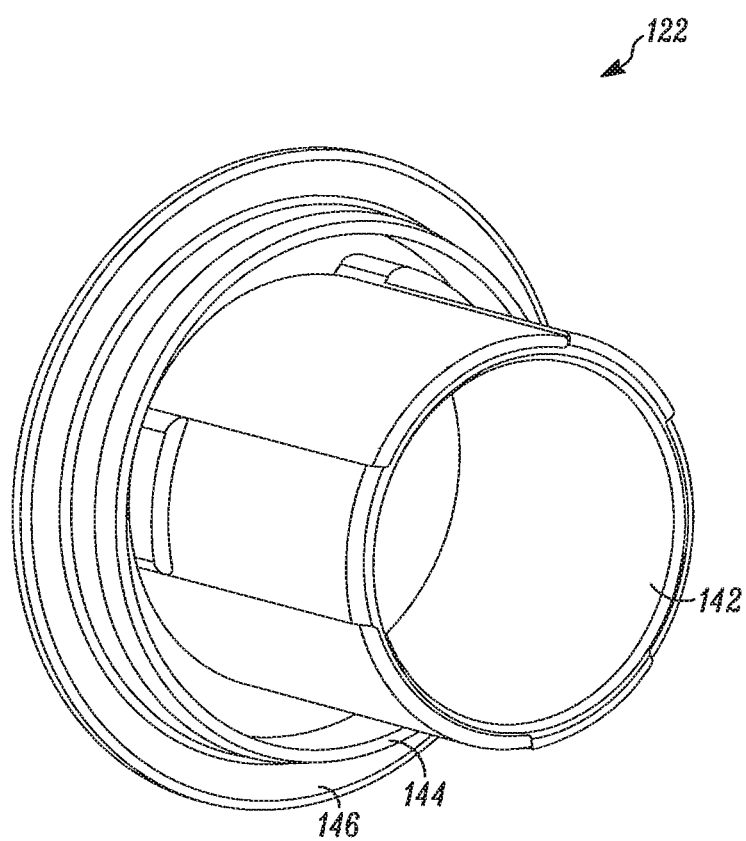
FIG. 7 is a rear perspective view of the oscillation member shown in the embodiment of FIG. 3.

A rear perspective view of the oscillation member 122 is shown in FIG. 7. The post 142 is configured for positioning about the glide surface 126, as shown in FIG. 3, so that the post 142 is in sliding contact with the glide surface 126. When the post 142 is positioned about the glide surface 126, the oscillation member 122 is substantially limited to reciprocal movement about the central axis of the oscillation member 122. As shown in FIGS. 3 and 7, the glide surface 126 and the post 142 are shaped as hollow cylinders, and the post 142 is sized to fit within the glide surface 126. However, the glide surface 126 and the post 142 may have any shape, and the glide surface 126 may be alternatively sized to fit within the post 142. The oscillation member 122 also includes a skirt 144 for aligning a biasing member, such as the coil spring 124, about the oscillation member 122 when the OPEP device 100 is assembled.

Referring to FIG. 3, the coil spring 124 is positioned to extend from the housing 102 and contact a lower surface 146 of the oscillation member 122. The coil spring 124 is positioned to bias the oscillation member 122 into engagement with the deformable restrictor member 120. Similar to the deformable restrictor member 120 and the oscillation member 122, the coil spring 124 may be selectively replaced with other springs have a different rigidity or number of coils to achieve the desired operating conditions for the prescribed OPEP treatment.

To administer OPEP therapy using the OPEP device 100 descried above, a user begins by exhaling into the mouthpiece 112. In doing so, an exhalation flow path 148 is defined between the chamber inlet 114 and the at least one chamber outlet 116. The exhalation pressure at the chamber inlet 114 represents a function of the flow of exhaled air permitted to traverse the exhalation flow path 148 and exit the OPEP device 100 through the chamber outlet 116. As the exhalation pressure at the chamber inlet 114 changes, an equal back pressure is effectively transmitted to the respiratory system of the user.

As shown in FIG. 3, prior to using the OPEP device 100, the oscillation member 122 is biased to an engaged position, where the deformable restrictor member 120 is in contact with the oscillation member 122. In the engaged position, the exhalation flow path 148 is substantially restricted by the deformable restrictor member 120 and the oscillation member 122. As a user exhales into the OPEP device 100, an initial exhalation pressure at the chamber inlet 114 begins to increase, as only a fraction of the exhaled air is permitted to flow along the exhalation flow path 148 through the at least one channel 143 on the oscillation member 122. As the exhalation pressure increases at the chamber inlet 114 to an intermediate pressure, the deformable restrictor member 120 begins to expand under the force of the increased pressure. As the deformable restrictor member 120 expands, the lower portion 136 moves in an outward direction, toward the oscillation member 122. In the engaged position, however, the outward movement of the lower portion 136 is resisted by the oscillation member 122, which is biased against the deformable restrictor member 120 by the coil spring 124. As the exhalation pressure continues to increase, the deformable restrictor member 120 continues to deform until a maximum point of expansion is obtained. When the deformable restrictor member 120 obtains its maximum expansion, the exhalation pressure is also at a maximum pressure.

At the maximum point of expansion, the increasing exhalation pressure causes the deformable restrictor member 120 to quickly retract, ultimately returning to its natural shape. As the deformable restrictor member 120 retracts, the deformable restrictor member 120 and the oscillation member 122 move to a disengaged position, where the deformable restrictor member 120 is not in contact with the oscillation member 122. At that time, exhaled air is permitted to flow substantially unrestricted along the exhalation flow path 148 from the chamber inlet 114 to the chamber outlet 116. Because the retraction of the deformable restrictor member 120 is quicker than the movement of the oscillation member 122 under the biasing force of the coil spring 124, the deformable restrictor member 120 and the oscillation member 122 remain in the disengaged position for a short period of time, during which the exhalation pressure at the chamber inlet 114 decreases. Depending on multiple variables, including the elasticity of the deformable restrictor member 120, the biasing force of the coil spring 124, and the exhalation flow rate, the deformable restrictor member 120 and the oscillation member 122 may remain in the disengaged position for only a fraction of a second.

After the deformable restrictor member 120 returns to its natural shape, the oscillation member 122, under the biasing force of the coil spring 124, moves back into an engaged position with the deformable restrictor member 120. Then, as a user continues to exhale, the exhalation pressure at the chamber inlet 114 begins to increase, and the cycle described above is repeated. In this way, the exhalation pressure at the chamber inlet 114 oscillates between a minimum and a maximum so long as a user continues to exhale into the OPEP device 100. This oscillating pressure is effectively transmitted back to the respiratory system of the user to provide OPEP therapy.

Figure 8:
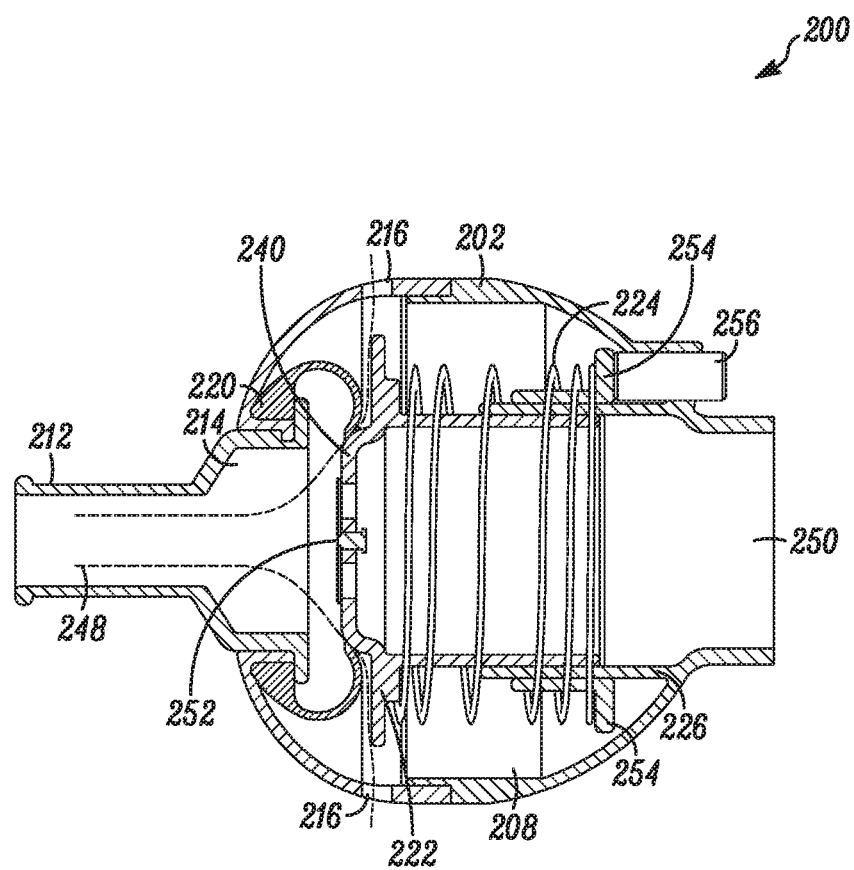
FIG. 8 is a cross-sectional side view of a second embodiment of an OPEP device, showing a deformable restrictor member and an oscillation member in an engaged position.

A cross-sectional side view of a second embodiment of an OPEP device 200 is shown in FIG. 8. Like the OPEP device 100, a housing 202 of the OPEP device 200 encloses a deformable restrictor member 220, an oscillation member 222, a coil spring 224, and a glide surface 226. The OPEP device 200 also includes a mouthpiece 212, a chamber inlet 214, a chamber outlet 216, and has an exhalation flow path 248 defined therebetween.

The OPEP device 200 further comprises an adjustment plate 254 for selectively moving an end of a biasing member, such as the coil spring 224, to adjust the amount of bias. The adjustment plate 254 is connected to at least one thumb screw 256 extending from the adjustment plate 254 to a location outside the housing 202. In this way, a user may rotate the at least one thumb screw 256 in one direction to move both the adjustment plate 254 and an end of the coil spring 224 toward the oscillation member 222, thereby increasing the bias. A user may rotate the at least one thumb screw 256 the opposite direction to decrease the bias. By changing the amount of bias, a user may selectively increase or decrease the resistance the oscillation member 222 applies against the deformable restrictor member 220 while in the engaged position. A change in the bias also changes the rate at which the oscillation member 222 moves from the engaged position to the disengaged position, and back to the engaged position, during the administration of OPEP therapy.

Figure 9:
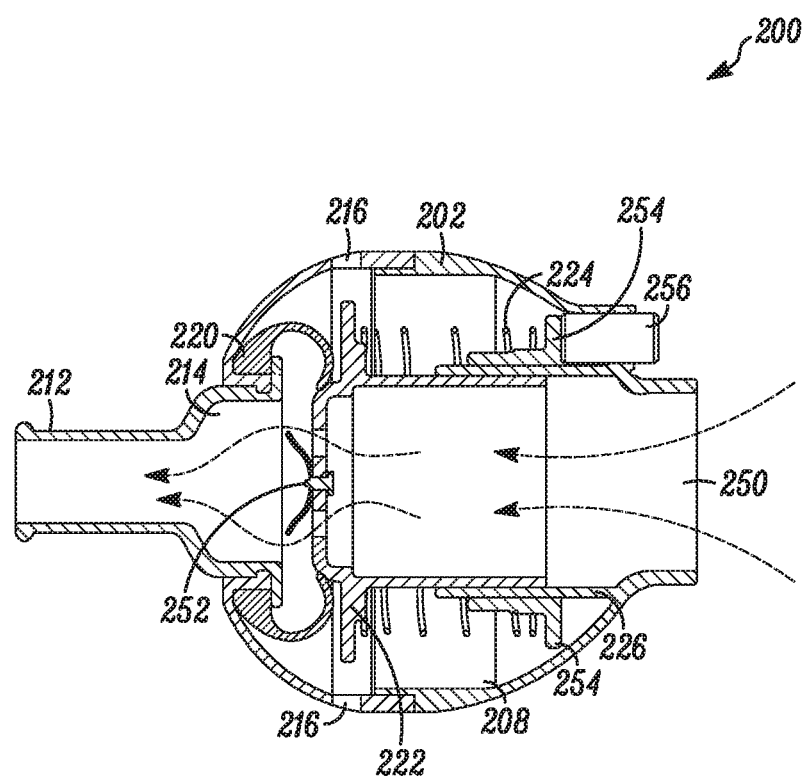
FIG. 9 is a cross-sectional side view of the embodiment of FIG. 8, showing the flow of air upon a user's inhalation.
Figure 10:
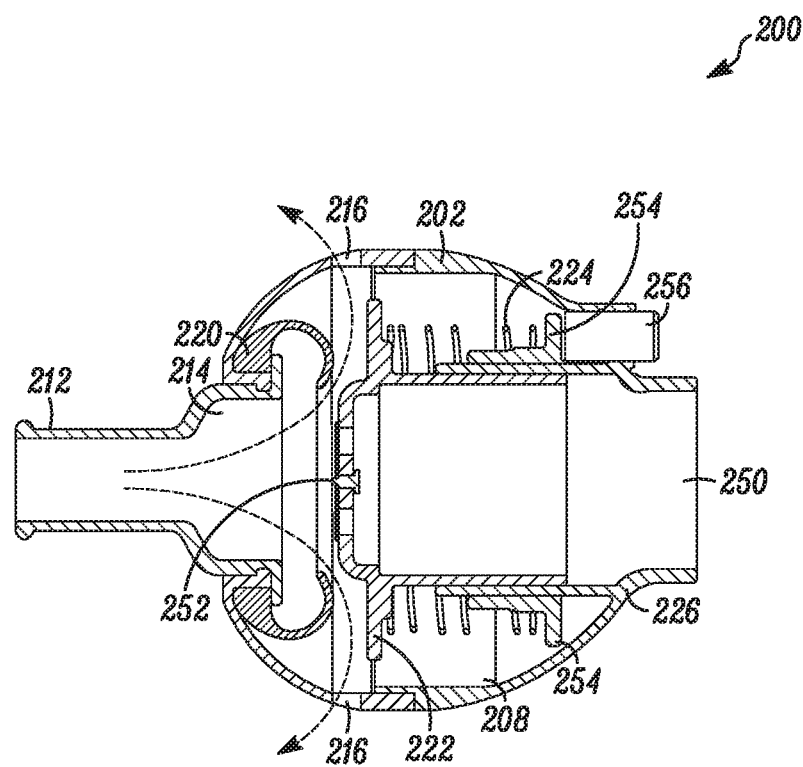
FIG. 10 is a cross-sectional side view of the embodiment of FIG. 8, showing the flow of air upon a user's exhalation.

The OPEP device 200 shown in FIG. 8 further comprises a respiratory portal 250 and a one-way valve 252 positioned on the oscillation member 222. The oscillation member 222 shown in FIG. 8 omits the at least one channel and has a substantially flat contact surface 240 to accommodate the one-way valve 252. The one-way valve 252 is configured to open as a user inhales, and permit air to enter the chamber 208 from the respiratory portal 250, as shown in FIG. 9. In contrast, the one-way valve 252 is closed during exhalation, as seen at one point during the administration of OPEP therapy in FIG. 10, when the deformable restrictor member 220 and the oscillation member 222 are in the disengaged position.

Figure 11:
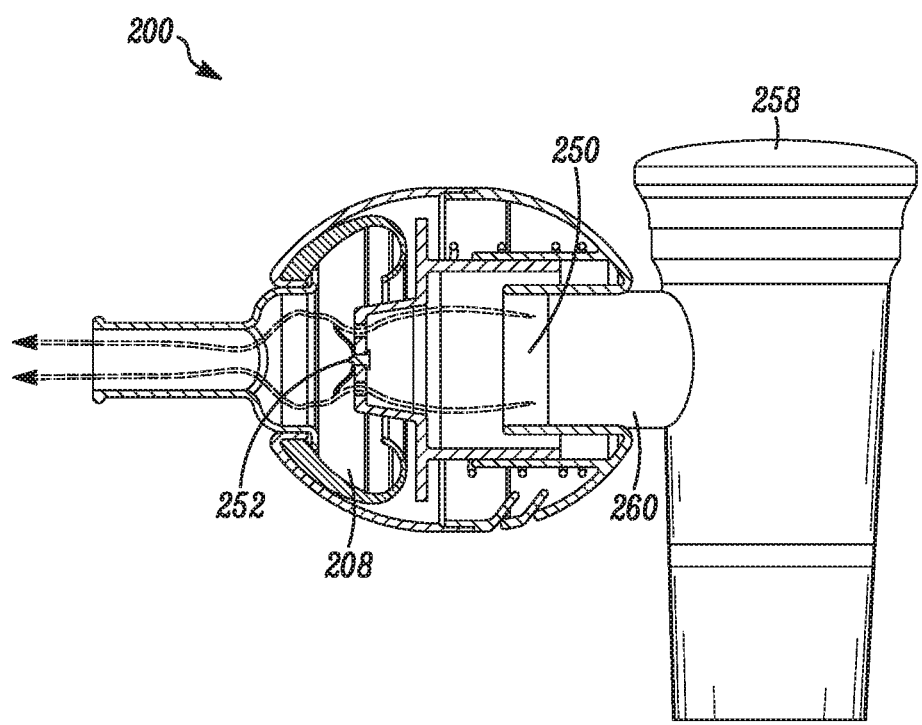
FIG. 11 is a cross-sectional side view of an OPEP device connected to a nebulizer, showing the flow of an aerosol medicament upon a user's inhalation.

Referring to FIG. 11, the respiratory portal 250 of the OPEP device 200 is also configured to receive an aerosol outlet 260 of a nebulizer 258. The nebulizer 258 may be removably connected to the OPEP device 200 by any suitable means for the combined administration of OPEP and aerosol therapies. Any of a number of commercially available nebulizers may be used with the OPEP device 200. One suitable nebulizer is the AeroEclipse® II breath actuated nebulizer available from Trudell Medical International of London, Canada. Descriptions of suitable nebulizers may be found in U.S. Pat. No. 5,823,179, the entirety of which is hereby incorporated by reference herein.

Figure 12:
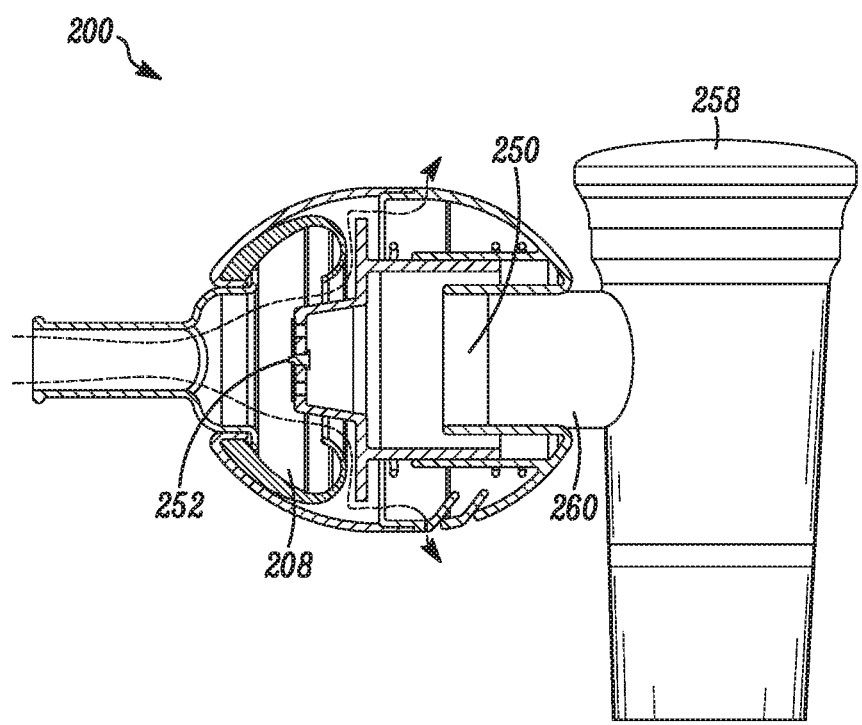
FIG. 12 is a cross-sectional side view of the OPEP device and nebulizer of FIG. 11, showing the flow of air upon a user's exhalation; and, FIG. 13 is a cross-sectional rear perspective view of a third embodiment of an OPEP device having a biasing member comprised of at least one pair of opposing magnets.

In this configuration, a user receives aerosol therapy upon inhalation. As seen in FIG. 11, when a user inhales, the one-way valve 252 opens, and an aerosol medicament is drawn from the aerosol output 260, through the respiratory portal 250 and the chamber 208, and into the respiratory system of the user. In contrast, OPEP therapy is delivered upon exhalation. As seen in FIG. 12, when a user exhales, the one-way valve 252 closes, the aerosol medicament is contained within the respiratory portal 250, and the OPEP device 200 is able to deliver OPEP therapy in accordance with the method described above.

Figure 13:
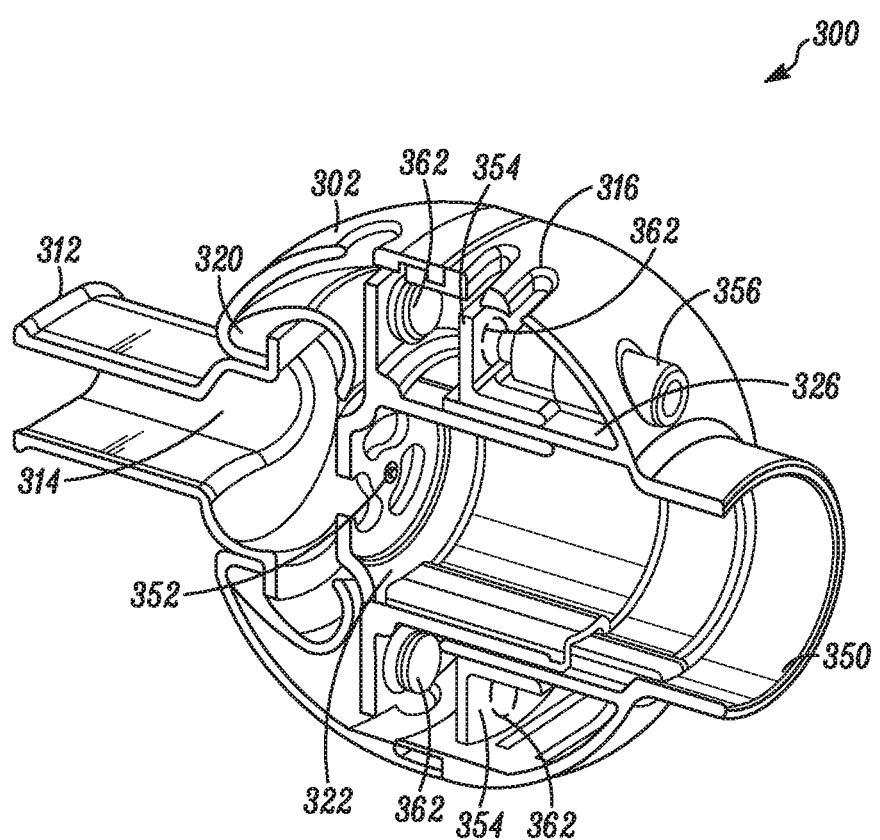

A cross-sectional perspective view of a third embodiment of an OPEP device 300 is shown in FIG. 13. In general, a housing 302 of the OPEP device 300 encloses a deformable restrictor member 320, an oscillation member 322 having a one-way valve 352, a glide surface 326, and an adjustment plate 354. The OPEP device 300 also includes a mouthpiece 312, a chamber inlet 314, a chamber outlet 316, and a respiratory portal 350.

The OPEP device 300 is different from the OPEP device 200 in that it includes a biasing member comprised of at least one pair of magnets 362. For each pair of the at least one pair of magnets 362, one magnet is positioned on the oscillation member 322 and another magnet is positioned on the adjustment plate 354. The magnets in each pair have opposing polarities. As such, the oscillation member 322 is biased by the at least one pair of magnets 362 into the engaged position with the deformable restrictor member 320.

During the administration of OPEP therapy, the at least one pair of magnets 362 functions in the same manner as the coil spring, as discussed above. Specifically, as a user exhales into the OPEP device 300 and the deformable restrictor member 320 expands, the at least one pair of magnets 362 resist the movement of oscillation member 322. After the deformable restrictor member 320 has reached its maximum point of expansion and quickly returned to its natural shape, the at least one pair of magnets 362 bias the oscillation member 322 from the disengaged position back to the engaged position. Furthermore, like the OPEP device 200, the amount of bias supplied by the at least one pair of magnets 362 may be adjusted by rotating the at least one thumb screw 356, thereby moving the adjustment plate 354 and the magnets positioned thereon closer to the magnets positioned on the oscillation member 322.

The foregoing description of the inventions has been presented for purposes of illustration and description, and is not intended to be exhaustive or to limit the inventions to the precise forms disclosed. It will be apparent to those skilled in the art that the present inventions are susceptible of many variations and modifications coming within the scope of the following claims.

What is claimed is:

1. An oscillating positive expiratory pressure apparatus comprising:
   a housing defining a chamber,
   a chamber inlet configured to receive exhaled air into the chamber;
   a chamber outlet configured to permit exhaled air to exit the chamber;
   a respiratory portal configured to receive an aerosol medicament into the chamber from a nebulizer configured to deliver aerosol therapy; and,
- a one-way valve configured to permit the aerosol medicament to enter the chamber;
- an inhalation flow path defined between the one-way valve and the chamber inlet; and,
- a moveable oscillation member positioned in the inhalation flow path;
- wherein the one-way valve is configured to remain closed during administration of oscillating positive expiratory pressure therapy, and is configured to open when the aerosol medicament is received into the chamber, thereby allowing a user to perform both oscillating positive expiratory pressure therapy and aerosol therapy during a respiratory cycle.

2. The oscillating positive expiratory pressure apparatus of claim 1, wherein the one-way valve is configured to remain closed during a period of exhalation.

3. The oscillating positive expiratory pressure apparatus of claim 1, wherein the one-way valve is configured to open during a period of inhalation.

4. The oscillating positive expiratory pressure apparatus of claim 1, wherein the inhalation flow path defined between the one-way valve and the chamber inlet is substantially unobstructed.

5. The oscillating positive expiratory pressure apparatus of claim 1, wherein the one-way valve is positioned on the oscillation member.

6. The oscillating positive expiratory pressure apparatus of claim 1, wherein the moveable oscillation member comprises a substantially flat contact surface.

7. The oscillating positive expiratory pressure apparatus of claim 1, wherein the moveable oscillation member comprises a hemispherical contact surface.

8. The oscillating positive expiratory pressure apparatus of claim 1, further comprising a mouthpiece in fluid communication with the chamber inlet, wherein the mouthpiece has a cross-sectional area greater than the cross-sectional area of the chamber inlet.

9. The oscillating positive expiratory pressure apparatus of claim 1 further comprising a restrictor member, wherein the restrictor member and the oscillation member are configured to move relative to one another between an engaged position, where the oscillation member is in contact with the restrictor member and a disengaged position, where the oscillation member is not in contact with the restrictor member.

10. The oscillating positive expiratory pressure apparatus of claim 9 further comprising a biasing member positioned to bias the restrictor member and the oscillation member to the engaged position.

11. The oscillating positive expiratory pressure device of claim 10, wherein the biasing member comprises a spring.

12. The oscillating positive expiratory pressure device of claim 10, wherein the biasing member comprises at least one pair of magnets, a first magnet of the at least one pair of magnets being connected to the oscillation member and a second magnet of the at least one pair of magnets being connected to the housing.

13. The oscillating positive expiratory pressure apparatus of claim 10, wherein the position of the biasing member is selectively moveable to adjust the amount of bias.

14. The oscillating positive expiratory pressure apparatus of claim 9, wherein the oscillation member further comprises at least one channel adapted to permit air to flow past the restrictor member when the oscillation member and the restrictor member are in the engaged position.

15. An oscillating positive expiratory pressure apparatus comprising:
- a housing defining a chamber;
- a chamber inlet configured to receive exhaled air into the chamber;
- a chamber outlet configured to permit exhaled air to exit the chamber;
- a mouthpiece in fluid communication with the chamber inlet,
- a one-way valve configured to permit air outside the chamber to enter the chamber;
- an inhalation flow path defined between the one-way valve and the mouthpiece;
- an exhalation flow path defined between the chamber inlet and the chamber outlet;

a restrictor member; and, a moveable oscillation member positioned in the inhalation flow path;

wherein the restrictor member and the oscillation member are configured to move relative to one another during a period of exhalation repeatedly between an engaged position, where the flow of exhaled air along the exhalation flow path is restricted and a disengaged position, where the flow of exhaled air along the exhalation flow path is less restricted; and, wherein the one-way valve is configured to open during a period of inhalation, and close during the period of exhalation.

16. The oscillating positive expiratory pressure apparatus of claim 15, wherein the air that enters the chamber through the one-way valve comprises an aerosol medicament.

17. The oscillating positive expiratory pressure apparatus of claim 16, wherein the one-way valve is positioned on the oscillation member.

18. The oscillating positive expiratory pressure apparatus of claim 16, wherein the inhalation flow path is substantially unobstructed between the one-way valve and the chamber inlet.

19. The oscillating positive expiratory pressure device of claim 15, wherein a cross-sectional area of the mouthpiece is greater than a cross-sectional area of the chamber inlet.

* * * * *

UNITED STATES PATENT AND TRADEMARK OFFICE
CERTIFICATE OF CORRECTION

| | | |
|---|---|---|
| PATENT NO. | : 11,865,254 B2 | Page 1 of 1 |
| APPLICATION NO. | : 16/853089 | |
| DATED | : January 9, 2024 | |
| INVENTOR(S) | : Jerry Grychowski and Martin P. Foley | |

It is certified that error appears in the above-identified patent and that said Letters Patent is hereby corrected as shown below:

In the Claims

Column 11, Line 18, Claim 17, delete "16" and replace with --15--.

Column 11, Line 21, Claim 18, delete "16" and replace with --15--.

Signed and Sealed this
Twenty-seventh Day of February, 2024

*Katherine Kelly Vidal*

Katherine Kelly Vidal
*Director of the United States Patent and Trademark Office*